(12) United States Patent
Williams et al.

(10) Patent No.: US 10,052,621 B2
(45) Date of Patent: Aug. 21, 2018

(54) DEHYDROGENATION OF NEAT FORMIC ACID

(71) Applicant: UNIVERSITY OF SOUTHERN CALIFORNIA, Los Angeles, CA (US)

(72) Inventors: Travis J. Williams, Los Angeles, CA (US); Jeff Joseph A. Celaje, Arcadia, CA (US); Zhiyao Lu, Duarte, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/210,350

(22) Filed: Jul. 14, 2016

(65) Prior Publication Data

US 2017/0014817 A1   Jan. 19, 2017

Related U.S. Application Data

(60) Provisional application No. 62/192,423, filed on Jul. 14, 2015.

(51) Int. Cl.
| | | |
|---|---|---|
| C07F 15/00 | (2006.01) | |
| B01J 31/22 | (2006.01) | |
| C07C 51/377 | (2006.01) | |

(52) U.S. Cl.
CPC ......... *B01J 31/2295* (2013.01); *C07C 51/377* (2013.01); *C07F 15/0033* (2013.01)

(58) Field of Classification Search
CPC .. B01J 31/2295; C07F 15/0033; C07C 51/377

(Continued)

(56) References Cited

U.S. PATENT DOCUMENTS

2012/0201744 A1    8/2012   Williams et al.

FOREIGN PATENT DOCUMENTS

WO     2016/057661 A1    4/2016

OTHER PUBLICATIONS

Greenburg et al., Dalton Transactions, vol. 43, No. 42, pp. 15990-15996 (2014).*

(Continued)

*Primary Examiner* — Pancham Bakshi
(74) *Attorney, Agent, or Firm* — Brooks Kushman P.C.

(57) ABSTRACT

A formic acid decomposition catalyst system includes metal-ligand complexes having formula 1:

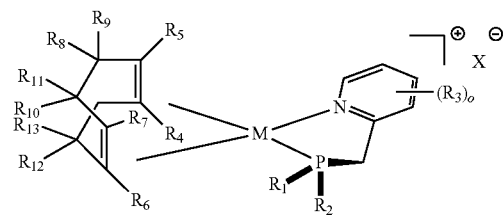

(1)

wherein M is a transition metal; $R_1$, $R_2$ are independently $C_{1-6}$ alkyl groups; o is 1, 2, 3, or 4; $R_3$ are independently hydrogen, $C_{1-6}$ alkyl groups, $OR_{14}$, $NO_2$, or halogen; $R_4$, $R_5$, $R_6$, $R_7$, $R_8$, $R_9$, $R_{10}$, $R_{11}$, $R_{12}$, $R_{13}$, are independently hydrogen or $C_{1-6}$ alkyl groups; $R_{14}$ is a $C_{1-6}$ alkyl group; and $X^-$ is a negatively charge counter ion.

11 Claims, 4 Drawing Sheets

(58) Field of Classification Search
USPC .................................. 556/21, 22; 546/2
See application file for complete search history.

(56) References Cited

OTHER PUBLICATIONS

Perez (Chemical Society Reviews; 2008, 37, 2658-2667).*
Celaje, J.J.A. et al., "A prolific catalyst for dehydrogenation of neat formic acid," Nature Communications 7, Article No. 11308, Published Apr. 14, 2016, pp. 1-6.
Boddien A. et al., "Efficient dehydrogenation of formic acid using an iron catalyst," Science, 2011, v. 333, pp. 1733-1736.
Choi, J. et al., "Dehydrogenation and related reactions catalyzed by iridium pincer complexes," Chem. Rev. 2011, v. 111, pp. 1761-1779.
Gruber, S. et al., "Characterization and Reactivity Studies of Dinuclear Iridium Hydride Complexes Prepared from Iridium Catalysts with N,P And C,N Ligands Under Hydrogenation Conditions," Organometallics 2013, 32, pp. 4702-4711.
Mellone, I. et al., "Formic acid dehydrogenation catalyzed by ruthenium complexes bearing the tripodal ligans triphos and NP3," DaltonTrans. 2013, v. 42, pp. 2495-2501.
Morris, D.J. et al., "Insights into Hydrogen Generation from Formic Acid Using Ruthenium Complexes," Organometallics 2009, 28, pp. 4133-4140.
Wang, W-H. et al., "Chapter 10. Recent advances in transition metal-catalysed homogeneous hydrogenation of carbon dioxide in aqueous media," Hydrogenation, book edited by Iyad Karame, ISBN 978-953-51-0785-9, Published Oct. 10, 2012, pp. 250-268.
International Search Report dated Jan. 4, 2016 for PCT Appn. No. PCT/US2015/054483 filed Oct. 7, 2015, 6 pgs.
U.S. Appl. No. 15/517,701, filed Apr. 7, 2017, title: "Dehydrogenation of Neat Formic Acid", inventor: Williams et al., 64 pgs.
Non-Final Office Action dated May 4, 2018 for U.S. Appl. No. 15/517,701, filed Apr. 7, 2017, 22 pgs.

* cited by examiner

DEHYDROGENATION OF NEAT FORMIC ACID

CROSS-REFERENCE TO RELATED APPLICATIONS

This application claims the benefit of U.S. provisional application Ser. No. 62/192,423 filed Jul. 14, 2015, the disclosure of which is hereby incorporated in its entirety by reference herein.

STATEMENT REGARDING FEDERALLY SPONSORED RESEARCH OR DEVELOPMENT

The invention was made with Government support under Contract No. CHE-1054910 awarded by the National Science Foundation. The Government has certain rights to the invention.

TECHNICAL FIELD

In at least one aspect, the present invention is related to metal-ligand complexes that catalyze the decomposition of formic acid.

BACKGROUND

Many strategies for the conversion of solar energy into chemical bonds involve electrocatalytic (or photocatalytic) cleavage of water to form hydrogen and oxygen. The reducing equivalent, $H_2$, is thus an energy carrier because it can be re-oxidized, either by combustion to give heat or catalytically in a fuel cell to give electricity. There is a disabling problem with large-scale utilization of hydrogen as a fuel, since it is a gas under ambient conditions, thus limiting its volume energy density (0.013 MJ $l^{-1}$). As a result, physical methods based hydrogen storage technologies (compression, cryogenic liquefaction, adsorption) involve low capacity, high costs or safety issues [1]. Therefore, the discovery of highly weight-efficient strategies for on-demand hydrogen release from hydrogen-rich liquids has value. Formic acid (HCO2H, FA, 7.5 MJ $l^{-1}$) is a hydrogen carrier, owing to its ability to release hydrogen under mild conditions with only $CO_2$ as a by-product [1-6], which can then be recycled, in principle, to give a carbon-neutral fuel cycle [7-9].

To date, many efficient heterogeneous [10-22] and homogeneous [9, 23-38] catalysts for FA dehydrogenation have been developed. Heterogeneous catalysts have advantages of separability and reusability [11], while homogeneous catalysts are generally more efficient. The best turnover numbers (TONs) achieved in homogeneous catalysis are (1) 41M, by a catalyst system composed of [RuCl2(benzene)]2, the ligand diphenylphosphinoethane and a FA/Et3N adduct as substrate developed by Boddien et al. 9 and (2) 983,642, by a system composed of an iron pincer complex and LiBF4 developed by Bielinski et al. [35]. The highest turnover frequency achieved is 228,000 h_1 by an iridium catalyst developed by Hull et al. [27]. In heterogeneous catalysis, the highest TOF achieved is 7,256 h_1, by palladium nanoparticles immobilized on carbon nanospheres developed by Zhu et al. 22. Also, homogeneous catalysts generally are more selective, producing less carbon monoxide, a common byproduct of FA dehydrogenation. This is essential, because CO is a fuel cell catalyst poison. Still, no known system is stable and reactive through multiple uses, air and water tolerant, selective against CO formation, and functions in neat FA liquid. Each of these is critical to achieving a usable hydrogen generation system based on FA.

Accordingly, there is a need for improved catalyst systems for the dehydrogenation of formic acid.

SUMMARY

The present invention solves one or more problems of the prior art by providing in at least one embodiment, a formic acid decomposition catalyst system. The catalyst system includes metal-ligand complexes having formula 1:

(1)

wherein:
M is a transition metal;
$R_1$, $R_2$ are independently $C_{1-6}$ alkyl groups;
o is 1, 2, 3, or 4;
$R_3$ are independently hydrogen, $C_{1-6}$ alkyl groups, $OR_{14}$, $NO_2$, or halogen;
$R_4$, $R_5$, $R_6$, $R_7$, $R_8$, $R_9$, $R_{10}$, $R_{11}$, $R_{12}$, $R_{13}$, are independently hydrogen or $C_{1-6}$ alkyl groups;
$R_{14}$ is a $C_{1-6}$ alkyl group; and
$X^-$ is a negatively charge counter ion.

In another embodiment, a method of dehydrogenating formic acid is provided. The method includes a step of contacting the catalyst system including the metal-ligand complex having formula 1 with formic acid in the presence of a base. Advantageously, this step is performed substantially free of solvents other than formic acid. Molecular hydrogen is then collected from the reaction of formic acid with the complex 1.

The present example provides the first example of formic acid dehydrogenation using neat formic acid that proceeds with near perfect selectivity. The catalyst can be re-used without regeneration through multiple cycles. While many solutions are known for formic acid dehydrogenation, none has both the mild conditions and high selectivity while being tolerant of high formic acid concentrations with low base loading. Together, these findings make the catalyst system of the present invention capable of generating the highest wt % of $H_2$ from a formic acid reactor.

DETAILED DESCRIPTION

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups (e.g. $R_i$ where i is an integer) include alkyl, lower alkyl, $C_{1-6}$ alkyl, $C_{6-10}$ aryl, or $C_{6-10}$ heteroaryl; single letters (e.g., "n" or "o") are 1, 2, 3, 4, or 5; the presence of an ion implies the presence of a counterion; percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

The term "alkyl" refers to $C_{1-20}$ inclusive, linear (i.e., "straight-chain"), branched, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms.

Throughout this application, where publications are referenced, the disclosures of these publications in their entireties are hereby incorporated by reference into this application to more fully describe the state of the art to which this invention pertains.

Abbreviations:

"FA" is formic acid.

"TON" is turnover number.

In an embodiment, a formic acid dehydrogenation catalyst system is provided. The catalyst system includes a metal-ligand complex having formula 1 is provided:

wherein:

M is a transition metal;

$R_1$, $R_2$ are each independently alkyl groups (e.g., $C_{1-6}$ alkyl groups);

$R_3$ are each independently hydrogen, alkyl groups (e.g., $C_{1-6}$ alkyl groups), $OR_{14}$, $NO_2$, or halogen;

o is 1, 2, 3, or 4;

$R_4$, $R_5$, $R_6$, $R_7$, $R_8$, $R_9$, $R_{10}$, $R_{11}$, $R_{12}$, $R_{13}$, are each independently hydrogen or alkyl groups (e.g., $C_{1-6}$ alkyl groups);

$R_{14}$ is a $C_{1-6}$ alkyl group; and $X^-$ is a negatively charge counter ion such as halide or trifluoromethanesulfonate (OTf). Typically, the catalyst system also includes a base as a co-catalyst.

In a variation M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thalium, ytterbium, lutetium, hafnium, tantalum, tungsten, rhenium, osmium, iridium, gold, platinum, thallium, lead, bismuth, polonium, thorium, protactinium, uranium, neptunium, and plutonium. In a refinement, M is a transition metal selected from the group consisting of ruthenium, rhodium, iridium, and iron. In another refinement, M is iridium.

In another variation, $R_1$, $R_2$ are methyl, ethyl, butyl, n-propyl, isopropyl, n-butyl, sec-butyl, or t-butyl. In a refinement, $R_1$, $R_2$ are t-butyl.

In still another variation, the $R_3$ are each independently selected from the group consisting of hydrogen, methyl, ethyl, butyl, n-propyl, isopropyl, n-butyl, sec-butyl, or t-butyl. In a refinement, the $R_3$ are hydrogen.

In yet another variation, $R_4$, $R_5$, $R_6$, $R_7$, $R_8$, $R_9$, $R_{10}$, $R_{11}$, $R_{12}$, $R_{13}$, are each independently methyl, ethyl, butyl, n-propyl, isopropyl, n-butyl, sec-butyl, or t-butyl. In a refinement, the $R_4$, $R_5$, $R_6$, $R_7$, $R_8$, $R_9$, $R_{10}$, $R_{11}$, $R_{12}$, $R_{13}$ are each independently hydrogen.

In an refinement, the orgranometallic complex is described by formula 2:

(2)

Iridium complex 2 is an efficient and selective homogeneous catalyst for decomposition of neat formic acid into $H_2$ and $CO_2$.

In another embodiment, a formic acid dehydrogenation catalyst system is provided. The catalyst system includes a metal-ligand complex having formula 3 as provided:

(3)

wherein:
M is a transition metal;
$R_1$, $R_2$ are each independently alkyl groups (e.g., $C_{1-6}$ alkyl groups);
$R_1$, $R_2$ are each independently alkyl groups (e.g., $C_{1-6}$ alkyl groups);

$R_3$ are each independently hydrogen, alkyl groups (e.g., $C_{1-6}$ alkyl groups), $OR_{14}$, $NO_2$, or halogen;
o is 1, 2, 3, or 4;
$R_{14}$ is a $C_{1-6}$ alkyl group;
$R_{15}$ is a $C_{1-6}$ alkyl group; and
$X^-$ is a negatively charge counter ion such as halide or trifluoromethanesulfonate (OTf). Typically, the catalyst system also includes a base as a co-catalyst.

In a variation M for formula 3, is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thalium, ytterbium, lutetium, hafnium, tantalum, tungsten, rhenium, osmium, iridium, gold, platinum, thallium, lead, bismuth, polonium, thorium, protactinium, uranium, neptunium, and plutonium. In a refinement, M is a transition metal selected from the group consisting of ruthenium, rhodium, iridium, and iron. In another refinement, M is iridium.

In another variation for formula 3, $R_1$, $R_2$ are methyl, ethyl, butyl, n-propyl, isopropyl, n-butyl, sec-butyl, or t-butyl. In a refinement, $R_1$, $R_2$ are t-butyl.

In an refinement, the orgranometallic complex is described by formula 4:

(4)

where $R_{15}$ is H or methyl.

In another embodiment, a method of dehydrogenating formic acid is provided. The method includes a step of contacting the metal-ligand complex having formula 1 and in particular, formula 2 or formula 3 and in particular formula 4, with formic acid in the presence of a base. Advantageously, this step is performed substantially free of solvents other than formic acid (i.e., less than 1 weight percent of the combined weight of catalyst and formic acid). In a refinement, this step is performed with solvents other than formic acid in an amount less than, in increasing order of preference, 20 weight percent, 10 weight percent, 5 weight percent, 2 weight percent, 1 weight percent, 0.1 weight percent or 0.1 weight percent of the combined weight of the formic acid and complex having formula 1. Molecular hydrogen is then collected from the reaction of formic acid with the complex 1.

In a variation, the reaction using the organometallic comples having formulae 1-4 requires base as co-catalyst. The rate of dehydrogenation is approximately the same when 5% of $CaCO_3$, KOH, NaOH, $NaO_2CH$ (sodium formate), and LiOH are used. The reaction proceeds about twice as fast when 5% of $Na_2CO_3$ and $K_2CO_3$ are used. Any of these bases are rapidly converted to the corresponding metal formate, which comprises the bulk of the catalytic material and gives it its white color. Because this is part of the catalyst, it does not accumulate over time.

The following examples illustrate the various embodiments of the present invention. Those skilled in the art will recognize many variations that are within the spirit of the present invention and scope of the claims.

Results

Additional details regarding the results for the present invention are found in J. J. A. Celaje, Z. Lu, E. A. Kedzie, N. J. Terrile, J. N. Lo, and T. J. Williams, *A prolific catalyst for dehydrogenation of neat formic acid*, Nature Communications 7, Article number: 11308 doi:10.1038/ncomms11308 (14 Apr. 2016); the entire disclosure of which is hereby incorporated by reference.

Reactivity in FA Dehydrogenation.

Figure 1:
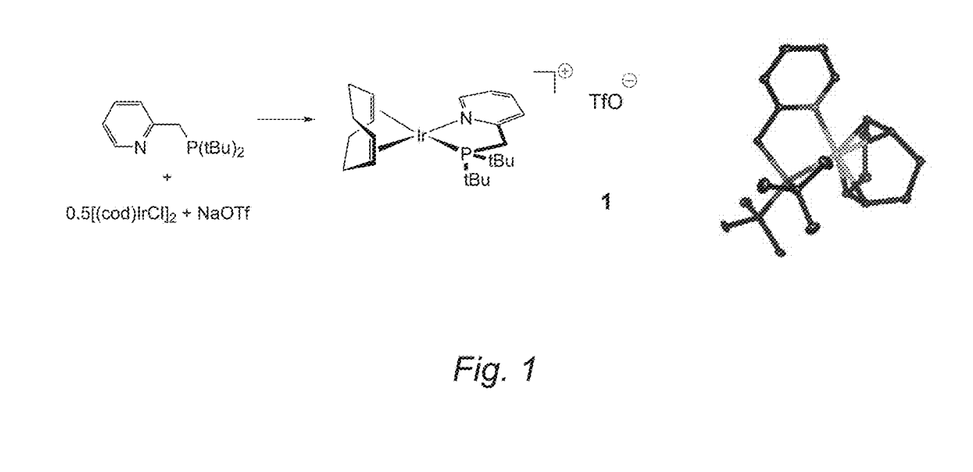
FIG. 1. Synthesis and structure of catalyst precursor cation 1. Elipsoids are drawn at the 50% probability level.

Complex 1, which is easily prepared from known materials (FIG. 1), decomposes FA (500 µl, 12.77 mmol) with $NaO_2CH$ co-catalyst (5 mol %) at 50 p.p.m. loading and 90° C., resulting in the production of 386 ml of gas (62% conversion; TON=12,530) after 13 h. The mass balance of FA condenses as a liquid in the reactor out of reach of the catalyst (vide infra). The rate of the reaction is constant through ca. 20% of conversion before it accelerates as FA disappears. At the end of the reaction, a pale orange solid (the catalyst system: an iridium complex and sodium formate) remains at the bottom of the reaction vessel. Recharging the reaction flask with FA and reheating to 90° C. results in continued $H_2$ production without any catalyst regeneration.

The reaction requires base as co-catalyst, but the source of the base is not specific: The reaction rates are similar when 5 mol % $NaO_2CH$, $KO_2CH$, KOH, NaOH, LiOH, or $nBu_4NOH$ or 2.5 mol % of $Na_2CO_3$ or $K_2CO_3$ is used. Any of these is converted rapidly to the corresponding formate, which comprises the bulk of the catalytic material and gives it its pale color. Moreover, water does not affect the rate of dehydrogenation significantly—the double logarithmic plot of water concentration versus rate of FA dehydrogenation yields a slope of 0.11(5).

The catalysts are air stable. Although dehydrogenation is slower when the catalysts are prepared in air, the system remains active, even when the solution is allowed to sit on the bench top for 2 weeks before dehydrogenation rates are measured. Under these conditions, the catalysts can be re-loaded in an air atmosphere and re-used repeatedly. For example, a reaction flask containing iridium 1 (6.1 mg, 8.9 mmol) and $NaO_2CH$ (185 mg, 2.72 mmol) was charged with FA through 50 cycles. In this experiment 28.85 l of gas was produced from 25 ml of FA, corresponding to a TON of 66,403 and 89% conversion. Note that these values exclude the FA liquid that condenses in the flask out of reach of the catalyst in each run and accounts for all mechanical leaks or engineering challenges in the laboratory-scale set-up. In a particular, representative single run, we converted FA (2 ml) to gaseous products in 97% conversion with 140 p.p.m. 1 and 280 p.p.m. sodium formate. Over the course of 50 loadings, we measured the initial rates and maximum turnover frequencies during certain runs (Table 1). Interestingly, these increased over the course of 10 cycles before slowing over time.

TABLE 1

Catalyst performance over iterative uses.

| Entry | Loading | Initial rate (µmol s$^{-1}$) | Maximum turnover frequency (h$^{-1}$) |
|---|---|---|---|
| 1 | 1$^{st}$ | 0.52 | 1,378 |
| 2 | 10$^{th}$ | 2.35 | 3,032 |
| 3 | 20$^{th}$ | 2.77 | 2,756 |
| 4 | 30$^{th}$ | 2.82 | 2,618 |
| 5 | 40$^{th}$ | 2.51 | 2,205 |
| 6 | 50$^{th}$ | 1.46 | 1,519 |

The iridium catalyst delivers very high TONs at low loading with repeated re-use. For example, we prepared in the drybox a reaction flask containing 1 (90 mg, 0.13 mmol) and $NaO_2CH$ (184 mg, 2.65 mmol) and repeatedly charged it with FA, which was decomposed until a pale yellow solid remained at the bottom of the flask. After 40 cycles over a period of four months, 13.71 l of gas was produced, which corresponds to a TON of 2.16 million. Although unoptimized, this is the best TON for a FA dehydrogenation catalyst known to date to our knowledge. Under these conditions, the maximum TOF was measured to be 3.7 s$^{-1}$.

The reaction is operationally simple. The catalytic materials are weighed out in a reactor, which is attached to a vent line for the gaseous products. Liquid FA is added, and the reaction is initiated by heating. Upon completion, the catalyst system remains as a pale-coloured precipitate at the bottom of the vessel for re-use.

Figure 2:
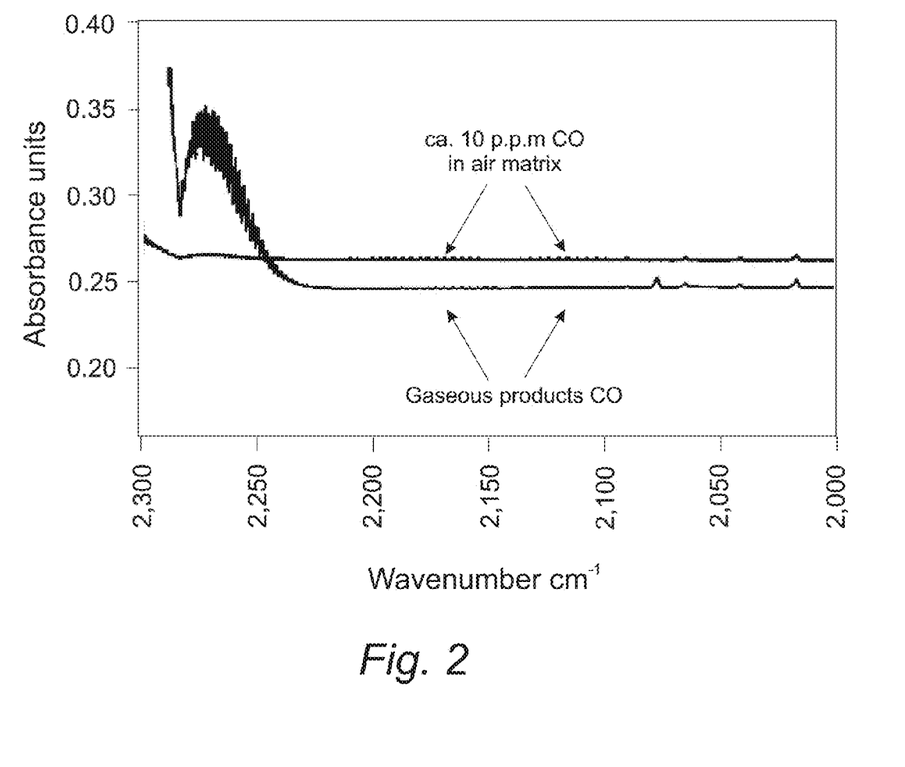
FIG. 2. Gas eluent stream infrared spectrum. The figure shows that compared to a prepared sample with 10 p.p.m. CO in air, the gaseous products from dehydrogenation of neat formic acid saturated in sodium formate contain <10 p.p.m. CO.

To be useful in fuel cells, FA decomposition must be selective for $H_2$ and $CO_2$ over $H_2O$ and CO, because CO is a poison for polymer electrolyte membrane (PEM) fuel cell catalysts such as platinum. The composition of gas produced from our conditions was determined by gas chromatography, which showed only $H_2$ and $CO_2$ (1:1 ratio) and no detectable CO (<1 part per thousand). However, further analysis of the product gas by infrared spectroscopy revealed that when the reaction is conducted using neat FA, CO is observed at a concentration near the detection limit of the gas chromatography. It is known that neat FA decomposes in the presence of concentrated acid [39] or at high temperatures to form $H_2O$ and CO [40,41]. We therefore hypothesized that much of the CO produced in our reaction conditions may be formed by thermal, uncatalysed decomposition pathways. Thus, we performed the dehydrogenation in the presence of a portion of water (10 v %), and observed that under these conditions the CO in the bulk gaseous products is <10 p.p.m. by infrared spectroscopy. Moreover, we hypothesized that the thermal decomposition of neat FA might be suppressed by running the reaction using higher sodium formate loading. Indeed, heating 1 ml of neat FA in 26 mg of the iridium precatalyst and 900 mg of sodium formate (50 mol %) to 90° C. for 2 h yields a product mixture with less than 10 p.p.m. CO (FIG. 2). A similarly low level of CO is observed when dehydrogenation is performed at 70° C. for 6 h. While these strategies for CO minimization are known in the FA literature, this collection of demonstrations enables practitioners to select the level of humidity and CO content in the reaction's gas eluent stream simply by adjusting the water and base loading in the FA supply. The optimum of these parameters might be different for any particular fuel cell application, but the reaction affords flexibility to adjust them.

The active catalyst is homogeneous is found on the basis of physical appearance, clean kinetics, tolerance of liquid mercury and proportional inhibition by phenanthroline [42].

Accordingly, the system exhibits the reactivity and selectivity advantages of homogeneous catalysis. Nonetheless, because the catalytic materials are deposited cleanly in the reactor at the end of the reaction, the system enjoys many of the catalyst separability and reusability benefits of heterogeneous conditions.

Mechanistic Studies.

Figure 3:
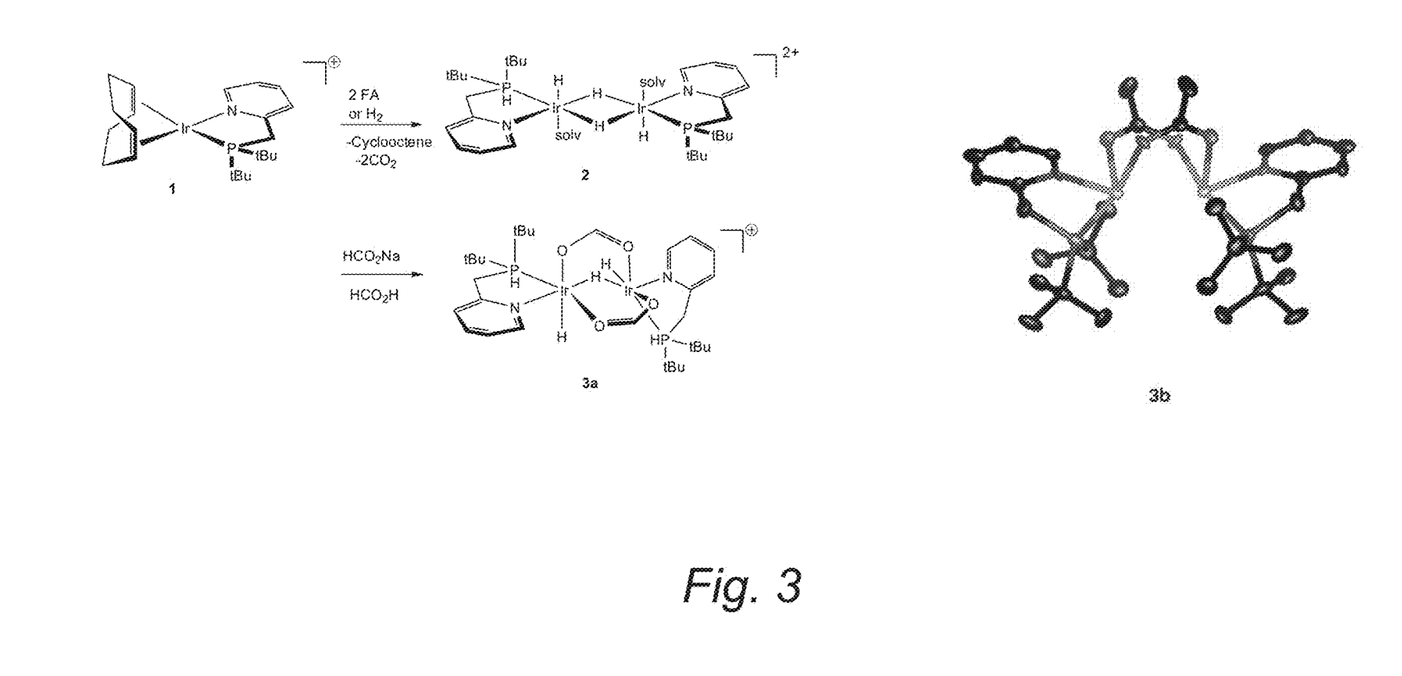
FIG. 3. Catalyst initiation and molecular structure of active catalyst homologue 3b. 3b={[(tBu$_2$PCH$_2$(2-py))Ir (H)]2($\mu^2$-H)($\mu^2$-κ,κ'-O$_2$CCH$_3$)$_2$}$^+$. Hydrogen atoms omitted. Ellipsoids are drawn at the 50% probability level. counterion, trifluoromethanesulfonate; solv, solvent.
Figure 4:
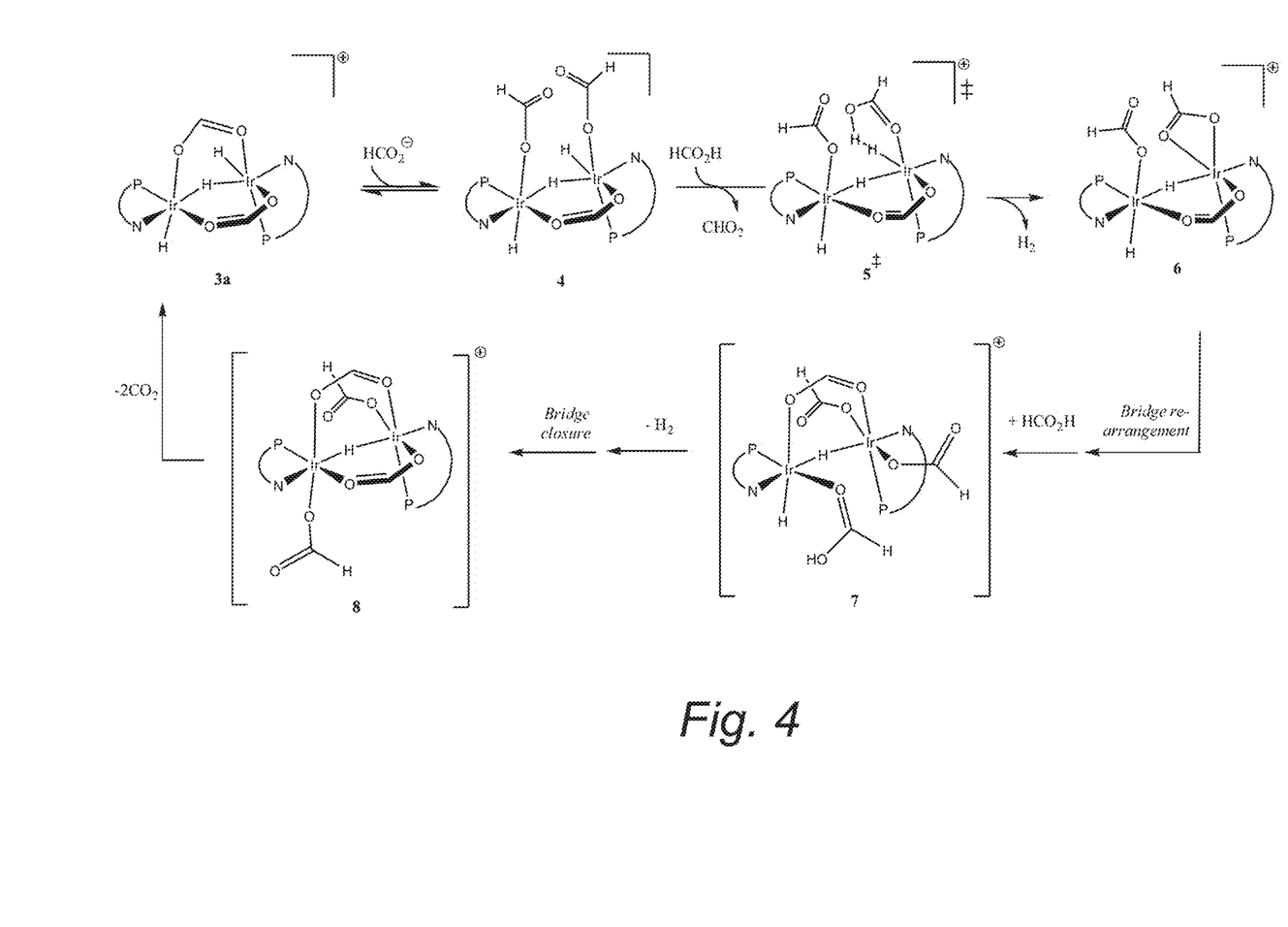
FIG. 4. Proposed mechanism of catalysis. Counterion, trifluoromethanesulfonate. ‡ Refers to a proposed transition state. The P—N ligand is 2-((di-tbutylphosphino)methyl)pyridine.

Equally remarkable as the reactivity of this new catalytic system is the unique, two-metal mechanism through which it operates. We used three approaches to gain insight into this mechanism: stoichiometric model reactions, reaction kinetics and isotope labelling studies. FIGS. 3 and 4 present a sketch of a possible mechanism for our system. Species 1 is a catalyst precursor from which an active catalyst is generated. To determine the nature of this active species, we conducted stoichiometric reactions of 1 (FIG. 3). Species 1 loses its cyclooctadiene ligand as cyclooctene in a solution of either $H_2$ or buffered FA and dimerizes to form 2. Complex 2 has analogy to $\{[(P—N)Ir(CH_2Cl_2)(H)]_2(\mu^2-H)_2\}^{2+}$ characterized by Pfaltz[43] (P—N=SimplePHOX). In buffered FA conditions, 2 is then converted to a formate-bridged species 3a. While this species is observable by NMR, it is not amenable to isolation in our hands. By contrast, its acetate homologue (3b) yielded to crystallization, which enabled determination of its structure (FIG. 3). Species 3a is relevant in catalysis: we observe it by NMR as the minor form of the working catalyst. We see a second, major resting species by NMR, which has a spectrum consistent with structure 4, featuring three differentiated metal hydride groups.

Kinetic isotope effect data indicate that both the C—H and O—H groups of FA are involved in (or before) the rate-determining transition state. Table 2 summarizes the reaction rates for four selectively labelled FA isotopologues. The combined isotope effect ($k_{CHOH}/k_{CDOD}$=6.5(2)) is comparable to the product of the average separate C—H and O—H isotope effects (6.5(4)). This is consistent with a mechanism by which bonds to proton and hydride are transformed in a single kinetically relevant step. Hydrogen loss from 4 involves protonation of an iridium hydride (which comes from FA's C—H group) by a FA group. Further, we observe that in a sample of FA-(O)-d1, NMR reveals H-D gas as the catalytic. A small portion of H2 is formed in the process of catalyst initiation, but none is detected during catalysis. This indicates that there is separation of proton and hydride groups throughout the mechanism and refutes the possibility of an iridium dihydride species in the mechanism, because such a species would be likely to enable proton/hydride scrambling via reversible reductive elimination of dihydrogen. This observation also shows that the reaction is irreversible at ambient pressure, so we assign the isotope effects as kinetic.

TABLE 2

Kinetic isotope effect data

| Compound | Krel | KIE (observed) | |
|---|---|---|---|
| $HCO_2H$ | 6.5 (2) | $k_{CHOH}/k_{CHOD}$ | 1.8 (3) |
| $HCO_2D$ | 3.6 (2) | $k_{CDOH}/k_{CDOD}$ | 1.65 (3) |
| $DCO_2H$ | 1.6 (2) | $k_{CHOH}/k_{CDOH}$ | 3.9 (2) |
| $DCO_2D$ | 1.00 (2) | $k_{CHOD}/k_{CDOD}$ | 3.6 (2) |
| | | $k_{CHOH}/k_{CDOD}$ | 6.5 (2) |

Conditions are 50 p.p.m. 1, 5 mol % base, 86° C.

Eyring analysis reveals activation parameters of $\Delta H\ddagger=+29.0(3)$ kcal $mol^{-1}$ and $\Delta S\ddagger=+16(1)$ eu ($\Delta H\ddagger=121(12)$ $kJmol^{-1}$). This strongly favorable entropy of activation is consistent with the release of at least one gaseous product in the rate-determining transition state. We expect that this is $H_2$ release in the conversion of 4 to 6 because of the strong isotope effects.

The observed rate law for FA dehydrogenation has rate~$[Ir]^1[base]^{0.5}[FA]^{-1}$, which is based on the slopes of double algorithmic plots recorded both in neat FA and dilute in tetraglyme solution (Table 3). This rate law requires that two sites of the catalyst are activated by a single equivalent of formate, thus causing half-order dependence on base. We propose a possible catalytic cycle in FIG. 4. After the first equivalent of $H_2$ is lost in the conversion of 4 to 6, a second equivalent forms from the iridium hydride on the complementary metal centre. We propose that the latter is more rapid than the former, and that the single equivalent of formate enables both by opening a formate bridge in dimer 3a. The rate law also has [Ir] first order, which indicates a dimeric iridium species that does not dissociate once formed. Inverse order in [FA] implies inhibition, but the origins of this inhibition are unclear. Acid is known to favour closure of carboxylate bridges in ruthenium species similar to ours [44], which enables several opportunities for FA inhibition in our mechanism. Moreover, FA has potential roles in the conversion of 4 and as solvent. We are currently studying this complex system of interactions.

TABLE 3

Reaction kinetics

| | Neat* | Solution*,† |
|---|---|---|
| [Ir] | 0.95(3)‡ | 0.96(4)∥ |
| [base] | 0.64(5)¶ | 0.44(2)# |
| [FA] | — | −0.94(9)** |

*Data were collected at 86° C. as an average of two runs.
†Tetraglyme was used as solvent. Base was delivered as (n-Bu)$_4$NOH to generate soluble (n-Bu)$_4$N(O$_2$$_{=CH}$).
‡Data were collected using 0.63M [NaO$_2$CH] (2.5 mol %) and [Ir] concentrations of 0.63, 1.86, 2.59, 3.25 and 4.41 mM.
∥Data were collecting using 13.2 mM [(n-Bu)$_4$N(O$_2$CH)] (5 mol %) and [Ir] concentrations of 0.066, 0.13, 0.20, 02.6 and 0.33 mM.
¶Data were collecting using 0.66 mM [Ir] and [NaO$_2$CH] concentrations of 0.26, 0.53, 1.06, 1.59, 2.11 and 2.65M.
Data were collected using 0.066 mM [I4] and [(n-Bu)$_4$N(O$_2$CH)] concentrations of 13.2, 26.4, 39.6, 52.8 and 66.0 mM.
**Data were collected using 0.026 [Ir], 13.2 mM [(n-Bu)$_4$N(O$_2$CH)] and [FA] concentrations of 265, 331, 398, 530 and 662 mM.

Methods

Synthesis of complex 1. In the drybox under nitrogen, 2-((di-t-butylphosphino)methyl)pyridine[45] (105.3 mg, 0.44 mmol) was dissolved in a dry vial in 5 ml of dry dichloromethane. In another vial containing a Teflon stir bar, chloro(1,5-cyclooctadiene)iridium(I) dimer (149.0 mg, 0.22 mmol) and sodium triflate (130 mg, 0.75 mmol) were suspended in 10 ml of dry dichloromethane. The suspension was stirred vigorously and then the phosphinopyridine solution was added slowly dropwise. The phosphinopyridine vial was rinsed with 5 ml of dichloromethane and added to the stirred suspension. After stirring for 1 h, the solution was filtered to remove the sodium chloride byproduct and the excess sodium triflate. The solvent was evaporated under reduced pressure to yield an orange glassy solid. A 5:1 mixture of dry hexanes/ethyl ether (10 ml) was added to the residue and then triturated by sonication. The hexane was decanted and the residue washed with an additional 10 ml of hexanes/ethyl ether. The pure iridium complex was dried under reduced pressure to give an orange solid (235 mg, 77.3%). Recrystallization from dichloromethane and toluene produced crystals suitable for X-ray crystallography.

Dehydrogenation Procedures.

The dehydrogenation of FA can generally be performed by preparing a stock solution of the catalysts. In the drybox, formate and the iridium precatalyst are dissolved in either FA or tetraglyme solvent. The resulting orange solution slowly turns pale yellow over the course of ca. 1 h. The solution is allowed to sit for several hours or overnight before the catalyst is used for dehydrogenation reactions.

Reactions Followed to Completion.

In the drybox, a 0.5-ml aliquot of a stock solution is transferred into a 5-ml high-pressure reaction flask possessing a side arm and a large-bore plug valve. The flask is then taken out of the drybox and connected to a vent line leading to a gas burette filled with oil (a eudiometer). To follow the reaction to completion, a 1,000-ml gas burette is used. The reaction flask is heated to 90° C. in an oil bath for ca. 15 min before opening the valve. The volume of gas produced over time is recorded. Some portion of the liquid FA vapourizes and re-condenses in the head space of the flask and gas evacuation tube, which prevents complete conversion.

Accurate Measurements of Initial Rates.

In the drybox, a 0.5-ml aliquot of a stock solution is transferred into a 5-ml reaction flask possessing a large-bore plug valve and a side arm. This flask is taken out of the drybox and the sidearm is connected to a three-way valve, which is connected to a nitrogen line and a 50-ml gas burette. The tubing and gas burette are purged with nitrogen for ca. 15 min. The reaction flask is then heated in an oil bath to 86° C. Because the oil bath temperature increases after initial heating, the mixture is heated for ca. 15 min before readings are taken to allow the temperature to equilibrate. The volume of gas formed over time was then recorded. The initial rate of FA decomposition (average of two runs) was obtained from a plot of moles of FA decomposed versus time (20 data points were obtained in each experiment).

Method of Initial Rates.

Because the rate of FA dehydrogenation is constant at the beginning of the reaction, we used the method of initial rates to obtain kinetics data to compare directly the dehydrogenation rates when different bases are utilized, to construct an Eyring plot, to measure kinetic isotope effects, and to determine the effect of water and of different poisons (that is, mercury and phenanthroline). Also, this method was used to study the reaction order in the iridium catalyst, the base and FA to determine the rate law.

Obtaining the X-Ray Structure of the Catalyst Homolog 3b.

In the drybox under nitrogen, complex 1 (10 mg, 14.9 mmol) was dissolved in 0.6 ml dichloromethane $d_2$ in a J-Young NMR tube. Dry acetic acid (8.6 ml, 149 mmol) was also added to this solution. The tube was then degassed, put under 1 atm head pressure of $H_2$ gas, and shaken. After ca. 5 min, a $^1H$ NMR spectrum of the crude reaction mixture was obtained, which confirmed the formation of 2. The solution was then poured into a dry 1-dram vial. Hexane was carefully layered on top of this dichloromethane solution, and the vial was left in a desiccator for 1 week. A crystal suitable for X-ray diffraction was isolated from the vial. Although the crystal of 3b is stable for days, the pure crystal of 3b re-dissolved in dichloromethane-$d_2$ appears to be in equilibrium with 2 and potentially any other form of the iridium complex.

Discussion

Embodiments of the invention provide a new catalytic system for the repeated conversion of FA to $CO_2$ and hydrogen. This has translation potential because it is the first known homogeneous system, to the best of our knowledge, to operate in neat FA, thus enabling far greater weight content of $H_2$ release than any other known catalyst for FA dehydrogenation. Moreover, it is the highest turnover system, because, in part, it can be re-used directly with FA substrate that is not rigorously purified or dried. We further propose a mechanism to account for kinetic, thermochemical, stoichiometric and labelling data that we have collected for the catalytic reaction. More detailed mechanistic studies, including computational investigation and ligand variation, are currently under way.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments, variations, and refinements may be combined to form further embodiments of the invention.

REFERENCES

1. Enthaler, S. Carbon dioxide—the hydrogen-storage material of the future? *ChemSusChem.* 1, 801-804 (2008).
2. Joo, F. Breakthroughs in hydrogen storage—formic acid as a sustainable storage material for hydrogen. *ChemSusChem.* 1, 805-808 (2008).
3. Grasemann, M. & Laurenczy, G. Formic acid as a hydrogen source—recent developments and future trends. *Energy Environ. Sci.* 5, 8171-8181 (2012).
4. Laurenczy, G. & Dyson, P. J. Homogeneous catalytic dehydrogenation of formic acid: progress towards a hydrogen-based economy. *J. Braz. Chem. Soc.* 25, 2157-2163 (2014).
5. Boddien, A. et al. M. Iron-catalyzed hydrogen production from formic acid. *J. Am. Chem. Soc.* 132, 8924-8934 (2010).
6. Czaun, M. et al. Hydrogen generation from formic acid decomposition by ruthenium carbonyl complexes. Tetraruthenium dodecacarbonyl tetrahydride as an active intermediate. *ChemSusChem.* 4, 1241-1248 (2011).
7. Tanaka, R., Yamashita, M. & Nozaki, K. Catalytic hydrogenation of carbon dioxide using Ir(III)-pincer complexes. *J. Am. Chem. Soc.* 131, 14168-14169 (2009).
8. Loges, B., Boddien, A., Junge, H. & Beller, M. Controlled generation of hydrogen from formic acid amine adducts at room temperature and application in H2/O2 fuel cells. *Angew. Chem. Int. Ed.* 47, 3962-3965 (2008).
9. Boddien, A., Loges, B., Junge, H. & Beller, M. Hydrogen generation at ambient conditions: application in fuel cells. *ChemSusChem.* 1, 751-758 (2008).
10. Zhou, X. et al. High-quality hydrogen from the catalyzed decomposition of formic acid by Pd—Au/C and Pd—Ag/C. *Chem. Commun.* 44, 3540-3542 (2008).
11. Huang, Y., Zhou, X., Yin, M., Liu, C. & Xing, W. Novel PdAu@Au/C core-shell catalyst: superior activity and selectivity in formic acid decomposition for hydrogen generation. *Chem. Mater.* 22, 5122-5128 (2010).
12. Tedsree, K. et al. Hydrogen production from formic acid decomposition at room temperature using a Ag—Pd core-shell nanocatalyst. *Nat. Nanotechnol.* 6, 302-307 (2011).
13. Gu, X., Lu, Z.-H., Jian, H.-L., Akita, T. & Xu, Q. Synergistic catalysis of metalorganic framework-immobilized Au—Pd nanoparticles in dehydrogenation of formic acid for chemical hydrogen storage. *J. Am. Chem. Soc.* 133, 11822-11825 (2011).

14. Bi, Q.-Y. et al. Efficient subnanometric gold-catalyzed hydrogen generation via formic acid decomposition under ambient conditions. *J. Am. Chem. Soc.* 134, 8926-8933 (2012).
15. Zhang, S., Metin, Ö., Su, D. & Sun, S. Monodisperse AgPd alloy nanoparticles and their superior catalysis for the dehydrogenation of formic acid. *Angew. Chem. Int. Ed.* 52, 3681-3684 (2013).
16. Wang, Z.-L. et al. An efficient CoAuPd/C catalyst for hydrogen generation from formic acid at room temperature. *Angew. Chem. Int. Ed.* 52, 4406-4409 (2013).
17. Kohsuke, M., Dojo, M. & Yamashita, H. Pd and Pd—Ag nanoparticles within a macroreticular basic resin: an efficient catalyst for hydrogen production from formic acid decomposition. *ACS Catal.* 6, 1114-1119 (2013).
18. Zhu, Z.-L., Tsumori, N. & Xu, Q. Sodium hydroxide-assisted growth of uniform Pd nanoparticles on nanoporous carbon MSC-30 for efficient and complete dehydrogenation of formic acid under ambient conditions. *Chem. Sci.* 5, 195-199 (2014).
19. Jian, K., Xu, K., Zou, S. & Cai, W.-B. B-Doped Pd catalyst: boosting room temperature hydrogen production from formic acid-formate solutions. *J. Am. Chem. Soc.* 136, 4861-4864 (2014).
20. Chen, Y., Zhu, Q.-L., Tsumori, N. & Xu, Q. Immobilizing highly catalytically active noble metal nanoparticles on reduced graphene oxide: a non-noble metal sacrificial approach. *J. Am. Chem. Soc.* 137, 106-109 (2015).
21. Zheng, Z., Tachikawa, T. & Majima, T. Plasmon-enhanced formic acid dehydrogenation using anisotropic Pd—Au nanorods studied at the single particle level. *J. Am. Chem. Soc.* 137, 948-957 (2015).
22. Zhu, Q.-L., Tsumori, N. & Xu, Q. Immobilizing extremely catalytically active palladium nanoparticles to carbon nanospheres: a weakly-capping growth approach. *J. Am. Chem. Soc.* 137, 11743-11748 (2015).
23. Gao, Y., Kuncheria, J., Puddephatt, R. J. & Yap, G. P. A. An efficient binuclear catalyst for decomposition of formic acid. *Chem. Commun.* 34, 2365-2366 (1998).
24. Fellay, C., Dyson, P. J. & Laurenczy, G. A viable hydrogen-storage system based on selective formic acid decomposition with a ruthenium catalyst. *Angew. Chem. Int. Ed.* 47, 3966-3968 (2008).
25. Himeda, Y. Highly efficient hydrogen evolution by decomposition of formic acid using an iridium catalyst with 4,4'-dihydroxy-2,2'-bipyridine. *Green Chem.* 11, 2018-2022 (2009).
26. Boddien, A. et al. Efficient dehydrogenation of formic acid using an iron catalyst. *Science* 333, 1733-1736 (2011).
27. Hull, J. G. et al. Reversible hydrogen storage using CO2 and a proton-switchable iridium catalyst in aqueous media under mild temperatures and pressures. *Nat. Chem.* 4, 383-388 (2012).
28. Barnard, J. H., Wang, C., Berry, N. G. & Xiao, J. Long-range metal-ligand bifunctional catalysis: cyclometallated iridium catalysts for the mild and rapid dehydrogenation of formic acid. *Chem. Sci.* 4, 1234-1244 (2013).
29. Mellone, I. et al. Formic acid dehydrogenation catalyse by ruthenium complexes bearing the tripodal ligands triphos and $NP_3$. *Dalton Trans.* 42, 2495-2501 (2013).
30. Oldenhof, S. et al. Base-free production of H2 by dehydrogenation of formic acid using an iridium-bis-METAMORPhos complex. *Chem. Eur. J.* 19, 11507-11511 (2013).
31. Sponholz, P., Mellmann, D., Junge, H. & Beller, M. Towards a practical setup for hydrogen production from formic acid. *ChemSusChem.* 6, 1172-1176 (2013).
32. Czaun, M. et al. Formic acid as a hydrogen storage medium: rutheniumcatalyzed generation of hydrogen from formic acid in emulsions. *ACS Catal.* 4, 311-320 (2014).
33. Manaka, Y. et al. Efficient $H_2$ generation from formic acid usine azole complexes in water. *Catal. Sci. Technol.* 4, 34-37 (2014).
34. Myers, T. & Berben, L. A. Aluminum-ligand cooperation promotes selective dehydrogenation of formic acid to $H_2$ and $CO_2$. *Chem. Sci.* 5, 2771-2777 (2014).
35. Bielinski, E. A. et al. Lewis acid-assisted formic acid dehydrogenation using a pincer-supported iron catalyst. *J. Am. Chem. Soc.* 136, 10234-10237 (2014).
36. Oldenhof, S., Lutz, M., de Bruin, B., van der Vlugt, J. I. & Reek, J. N. H. Dehydrogenation of formic acid by Ir-bisMETAMORPhos complexes: experimental and computational insight into the role of a cooperative ligand. *Chem. Sci.* 6, 1026-1034 (2015).
37. Thevenon, A., Frost-Pennington, E., Weijia, G., Dalebrook, A. F. & Laurenczy, G. Formic acid dehydrogenation catalyzed by Tris(TPPTS) ruthenium species: mechanism of the initial "fast" cycle. *ChemCatChem.* 6, 3146-3152 (2015).
38. Bertini, F., Mellone, I., Ienco, A., Peruzzini, M. & Gonsalvi, L. Iron(II) complexes of the linear rac-tetraphos-1 ligand as efficient homogeneous catalysts for sodium bicarbonate hydrogenation and formic acid dehydrogenation. *ACS Catal.* 5, 1254-1265 (2015).
39. DeRight, R. E. The decomposition of formic acid by sulfuric acid. *J. Am. Chem. Soc.* 55, 4761-4764 (1933).
40. Yu, J. & Savage, P. E. Decomposition of formic acid under hydrothermal conditions. *Ind. Eng. Chem. Res.* 37, 2-10 (1998).
41. Akiya, N. & Savage, P. E. Role of water in formic acid decomposition. *AIChE J.* 44, 405-415 (1998).
42. Hagen, C. M., Vieille-Petit, L., Laurenczy, G., Süss-Fink, G. & Finke, R. G. Supramolecular triruthenium cluster-based benzene hydrogenation catalysis:fact or fiction? *Organometallics* 24, 1819 (2005).
43. Gruber, S., Neuburger, M. & Pfaltz, A. Characterization and reactivity studies of dinuclear iridium hydride complexes prepared from iridium catalysts with N,P and C,N ligands under hydrogenation conditions. *Organometallics* 32, 4702-4711 (2013).
44. Morris, D. J., Clarkson, G. J. & Wills, M. Insights into hydrogen generation from formic acid using ruthenium complexes. *Organometallics* 28, 4133-4140 (2009).
45. Beddie, C., Wei, P. & Douglas, S. Titanium pyridylphosphinimide complexes: synthesis, structure, and ethylene polymerization catalysis. *Can. J. Chem.* 84, 755-761 (2006).

What is claimed is:
1. A metal-ligand complex having formula 1:

wherein:
M is a transition metal selected from the group consisting of ruthenium, rhodium, iridium, and iron;
$R_1$, $R_2$ are each independently $C_{1-6}$ alkyl groups;
$R_3$ are each independently hydrogen, $C_{1-6}$ alkyl groups, $OR_{14}$, $NO_2$, or halogen;
o is 1, 2, 3, or 4;
$R_4$, $R_5$, $R_6$, $R_7$, $R_8$, $R_9$, $R_{10}$, $R_{11}$, $R_{12}$, $R_{13}$, are each independently hydrogen or $C_{1-6}$ alkyl groups;
$R_{14}$ is a $C_{1-6}$ alkyl group; and
$X^-$ is a negatively charge counter ion.

2. The metal-ligand complex of claim 1 wherein M is iridium.

3. The metal-ligand complex of claim 1 wherein $R_1$, $R_2$ are each independently methyl, ethyl, butyl, n-propyl, iso-propyl, n-butyl, sec-butyl, or t-butyl.

4. The metal-ligand complex of claim 1 wherein the $R_3$ are hydrogen.

5. The metal-ligand complex of claim 1 wherein $R_4$, $R_5$, $R_6$, $R_7$, $R_8$, $R_9$, $R_{10}$, $R_{11}$, $R_{12}$, $R_{13}$ are each independently hydrogen.

6. The metal-ligand complex of claim 1 wherein $X^-$ is halide or trifluoromethanesulfonate (OTf).

7. The metal-ligand complex of claim 1 having formula 2:

where $OTf^-$ is trifluoromethanesulfonate.

8. A catalyst system including the metal-ligand complex of claim 1.

9. The catalyst system of claim 8 further includes a base as a co-catalyst.

10. A method of dehydrogenating formic acid with the metal-ligand complex of claim 1, the method comprising:
a step of contacting the metal-ligand complex having formula 1 with formic acid in the presence of a base.

11. The method of claim 10 wherein the metal-ligand complex having formula 1 is contacted with formic acid under solvent free conditions.

* * * * *